United States Patent [19]

Embrey et al.

[11] Patent Number: 5,017,382

[45] Date of Patent: May 21, 1991

[54] CONTROLLED RELEASE COMPOSITIONS (II)

[75] Inventors: Mostyn P. Embrey, Oxford, England; Neil B. Graham, Dunbartonshire, Scotland

[73] Assignee: National Research Development Corporation, London, England

[21] Appl. No.: 469,045

[22] Filed: Jan. 23, 1990

Related U.S. Application Data

[60] Division of Ser. No. 188,674, Apr. 29, 1988, Pat. No. 4,931,288, which is a continuation of Ser. No. 16,453, Feb. 24, 1987, abandoned, which is a continuation of Ser. No. 815,780, Jan. 3, 1986, abandoned, which is a continuation of Ser. No. 724,949, Apr. 22, 1985, abandoned, which is a continuation of Ser. No. 212,734, Nov. 5, 1980, abandoned.

[51] Int. Cl.$^5$ .............. A61K 9/14; A61K 31/74; A61F 9/70; A61F 13/00

[52] U.S. Cl. .................. 424/486; 424/422; 424/433; 424/436; 424/78; 424/443

[58] Field of Search .............. 424/486, 422, 433, 436, 424/78, 443

[56] References Cited

U.S. PATENT DOCUMENTS 3,822,238  7/1974  Blair .................... 528/904
3,975,350  8/1976  Hudgin et al. ............ 260/30.4 N

*Primary Examiner*—Thurman K. Page
*Assistant Examiner*—G. S. Kishore
*Attorney, Agent, or Firm*—Oblon, Spivak, McClelland, Maier & Neustadt

[57] ABSTRACT

A process for the preparation of a controlled release composition comprising a prostaglandin and a polymeric carrier therefor comprising residues having a ratio of number average molecular weight to functionality greater than 1,000 which comprise polyethylene oxide and are cross-linked through urethane groups.

30 Claims, No Drawings

CONTROLLED RELEASE COMPOSITIONS (II)

This application is a divisional of copending application Ser. No. 07/188,674, filed Apr. 29, 1988, now a U.S. Pat. No. 4,931,288 and which is a continuation of copending application Ser. No. 07/016,453, abandoned, filed Feb. 24, 1987, which is a continuation of copending application Ser. No. 06/815,780, filed Jan. 3, 1986, abandoned, which is a continuation of copending application Ser. No. 06/724,949, filed Apr. 22, 1985, abandoned, which is a continuation of copending application Ser. No. 06/212,734, filed Feb. 5, 1980, abandoned.

This invention relates to the formulation of active substances.

A considerable level of interest exists in the use of polymers as carriers in the formulation of various active substances. The main problem which arises with such a method of formulation is that of effecting release of the active substance from the polymer at an appropriate rate, and the polymer systems which have been proposed in the prior art are often not suited to the high level of control of release which is necessary for many applications such as the vaginal administration of pessaries for the induction of labour, as abortifacients, or in a contraceptive role.

It is an object of the present invention to provide a method of formulating a wide variety of active substances which utilises a polymer system having properties particularly suited to this purpose and selected for its particular value therein.

According to the present invention a controlled release composition comprises a prostaglandin and a polymeric carrier therefor comprising residues having a ratio of number average molecular weight to functionality greater than 1,000 which comprise polyethylene oxide and are cross-linked through urethane groups, preferably comprising a polymeric carrier comprising residues which comprise polyethylene oxide having a ratio of number average molecular weight to functionality greater than 1,000 and are cross-linked through urethane groups.

In our copending application we have described and claimed a controlled release composition comprising an active substance other than a prostaglandin and a polymeric carrier therefor comprising residues having a ratio of number average molecular weight to functionality greater than 1,000 which comprise polyethylene oxide and are cross-linked through urethane groups.

In this description the term equivalent weight is used as meaning the number average molecular weight ÷ functionality.

Residues comprising polyethylene oxide contain the repeat unit ($CH_2CH_2O$) and are conveniently prepared by the stepwise addition of ethylene oxide to a compound containing a reactive hydrogen atom therein, for example the hydrogen atom of an aromatic or especially an aliphatic hydroxy, carboxy, amino or mercapto group such as a phenolic group. Compounds of most interest contain two or more of such groups which may be the same or different, particular interest centering on carboxy and especially hydroxy groups. Preferred compounds for the preparation of the polyethylene oxides used in the present invention are thus polyhydroxy compounds containing particularly two but also three, four or, on occasion, even more hydroxy groups. In its simplest form, for example as prepared by the addition of ethylene oxide to ethylene glycol, polyethylene oxide has the difunctional structure $$HO-CH_2CH_2O)_nH$$

wherein n is an integer of varying size depending on the molecular weight of the polyethylene oxide, although various more complex forms may be prepared using other starting compounds and, in particular, forms of tri- or higher poly-functionality may be prepared using compounds containing more than two active hydrogen atoms.

However, the residues comprising the polyethylene oxide, typically prepared as aforesaid, may also comprise a minor amount of at least one additional component, for example a higher poly (alkylene oxide) such as polypropylene oxide or polybutylene oxide or a copolymerised higher alkylene oxide such as propylene oxide or polybutylene oxide. Typically, this minor amount will be small, suitably no more than 20%, preferably no more than 10% by weight or even less of the residue. Although the residues of equivalent weight greater than 1,000, preferably greater than 1,500, which comprise polyethylene oxide together with the urethane cross-linking component, do constitute that part of the polymeric carrier which is of particular importance and is responsible in large part for conferring to the polymeric carrier its desirable properties, it will be appreciated that the polymeric carrier may, nevertheless, also incorporate at least one additional component. Such additional components may include blocks of other polymers which are introduced therein, particularly other polyalkylene oxides, for example polypropylene oxides and polybutylene oxides or polyethylene oxide of equivalent weight less than 1,000.

Such co-polymers are, however, generally of rather less interest since polyethylene oxide possesses unique properties among the polyalkylene oxides arising from its hydrophilic character which render it of particular value in the present invention. It may also on occasion be desirable to effect chain extension and a consequent increase in the degree of swelling which is thereby obtained. Such chain extension may be effected by the incorporation of polyethylene oxide of equivalent weight less than 1,000 or other diols in the reaction mixture containing the high equivalent weight polyethylene oxide and the urethane cross-link precursors, for example low molecular weight aliphatic or aromatic dihydroxy compounds. As well as effecting swelling, such chain extension can have a beneficial effect on the physical strength of the polymer, both when wet and when dry.

It is an important feature of the polymers used in the present invention that they are cross-linked through urethane groups. Cross-linking is necessary to produce a polymer which is water swellable rather than water soluble and at the same time confers greater cohesion in the swollen polymer. Such cross linking gives a system which may be regarded, in theory, as having an infinite molecular weight, and a significant degree of cross-linking is required to achieve this. The preferred degree of cross-linking corresponds to a range of from three cross-linking points per residue comprising polyethylene oxide to one cross-linking point per ten such residues, particularly from one or two cross-linking points per residue to one cross-linking point per four or five residues. Alternatively, the preferred degree of cross-linking can in many cases be described as that leading to a molecular weight between cross-linking points of from about ½×(number average molecular weight of isocyanate+number average molecular weight of polyethylene oxide) to 10×(the sum of these molecular weights), particularly from ½ or 1× to 4 or 5×(the sum of these molecular weights).

While the polymeric carrier is required to swell rather than dissolve in water, it may contain a water-extractable fraction which is preferably a minor proportion by weight which can be as high as 30-40% by weight without detracting from the useful properties of the composition. More usually, however, the water-extractable fraction is 25% by weight or less. It will be appreciated, however, that it is the non-water extractable portion which is responsible in large part for the desirable release characteristics and, accordingly, it may be in many instances preferable to extract the polymer after preparation with water or a water/organic solvent mixture to substantially remove any extractable portion leaving, for example, no more than 5% or 10% by weight of such a portion. Thus, in the case of a composition for use in humans, it is desirable that substantially all water-extractable material is absent and the whole of the polymeric carrier in the composition is substantially insoluble. This is also desirable, in general, in order to give the best reproducibility of release for the drug or other active material contained in a composition.

The detailed method of cross-linking may vary quite widely although all methods basically involve the attachment of the residues comprising polyethylene oxide through a urethane group thus;

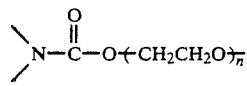

A preferred method comprises the reaction of polyethylene oxide of equivalent weight greater than 1,000, preferably greater than 1,500 with a poly-functional isocyanate, including aromatic di-isocyanates, such as 2,4 and/or 2,6 toluene di-isocyanate aliphatic di-isocyanates such as 1,6-hexamethylene di-isocyanate, isophorone di-isocyanate, 4,4'-dicyclohexyl methane di-isocyanate, and cyclohexylene 1,2- and 1,4-di-isocyanate, and araliphatic di-isocyanates such as 4,4'-diphenylmethane di-isocyanate, particularly aliphatic di-isocyanates. When reacting a di-isocyanate with a polyethylene oxide it is preferred to incorporate an additional polyfunctional compound in the reactants to give the desired cross-linking. Tri- or higher functional amines and particularly hydroxy compounds are conveniently used, including aliphatic triols such as 2-ethyl-2-hydroxymethyl propane-1,3-diol and 1,2,6-hexane-triol, aromatic triols such as phloroglucinol and pyrogallol, as well as araliphatic triols. The triol 1,2,6-hexane triol in particular has been found to give particularly attractive polymers, especially when used in connection with an araliphatic di-isocyanate such as 4,4'-diphenylmethane di-isocyanate or an aliphatic di-isocyanate. It will be appreciated, however, that a large class of low molecular weight polyols suitable for cross-linking in the polymers of the present invention is commercially available for the manufacture of rigid and flexible urethane foams. These materials are well known to those skilled in the art and comprise oxypropylated triols, tetrols and sugars, as well as some polyesters. In general, low molecular weight materials are preferred as the higher molecular weights can give compatibility problems which make the preparation of the polymeric carriers much more difficult.

As an alternative to the incorporation of an added reactant as described above, cross-linking may be effected by the use of a tri- or higher polyfunctional isocyanate, either in pure form or as a component of a commercial isocyanate preparation containing both di- and tri-isocyanates. A further method of effecting the cross-linking is through the use of an excess of isocyanate which will result in cross-linking through the formation of an allophanate group. A yet further method of cross-linking consists of the formation of a pre-polymer between the polyethylene oxide and a poly-functional, for example trifunctional, isocyanate which contains free isocyanate groups, the pre-polymer then being cross-linked through the action of water with the formation of substituted urea groups.

It will be appreciated that the polymer may be produced using various proportions of polyethylene oxide to polyfunctional isocyanate depending on the type of cross-linking intended and other components used. In general, however, the amount of an isocyanate used is often equal to from 0.8 to 2.5 times its equivalent weight for each equivalent weight of polyethylene oxide, particularly from 0.9 to 1.3 times the equivalent weight of the isocyanate. When using a trihydroxy compound or other similar cross-linking inducing agent various proportions of this may again be used, but the amount of triol is often equal to from one tenth of a mole to three moles for each mole of the polyethylene oxide, particularly from one fifth or one fourth of a mole to one or two moles of the triol. If a triol or similar compound is included in the reactants then the amount of isocyanate used is increased, this amount then corresponding in many cases to the ranges indicated above but with the amount being related both to the polyethylene oxide and to the triol, i.e. 0.8 to 2.5 times and particularly 0.9 to 1.3 times the equivalent weight of the isocyanate for each equivalent weight of polyethylene oxide and an amount in a similar range for each equivalent weight of the triol.

The particular value of the cross-linked polyethylene oxide polymers used in the formulation of controlled release compositions according to the present invention lies in two quite unexpected discoveries which have been made in respect of the properties of these polymers.

The first of these unexpected properties is the ability of the polymers to form crystalline hydrogels. The term hydrogel is used in this specification to denote a polymer which is swellable by water to form a gel rather than being dissolved to form a solution, the term being applicable to the polymer either in the unswollen or dry state or in the swollen or wet state. Crystalline linear polyethylene oxides are known but it is surprising that gels having a high level of crystallinity are obtainable from polymers used in the present invention in view of the cross-linking therein. The existence of crystallites in the gels not only makes a significant contribution to the strength of the swollen gels but is also believed to be responsible in large part for the advantageous pattern of release shown by the polymeric carriers in the dry form for an active substance incorporated therein and as discussed hereinafter. It should be stressed that complete crystallinity is not necessary and, indeed, is generally unobtainable in practice even for linear polyethylene oxides. Thus, for example, the polymer prepared from PEG 6,000, 2-ethyl-2-hydroxymethylpropane-1,3-diol (0.5 molar proportion) and 4,4-diphenylmethane di-isocyanate as described in detail hereinafter has a crystallinity in the dry form, as determined by differential scanning calorimetry, which is approximately 40% of that of high molecular weight commercial linear polyethylene oxide homopolymer, a level which is however surprising in itself. Preferred levels of crystallinity at 20° C. are 5% or more, for example 10 or 20% or more, referred to a similar standard.

The second of the unexpected properties of the polymers used according to the present invention is their property of exhibiting a very considerable level of syneresis when the temperature of the water swollen polymer is raided. It is known that at room temperature insoluble polyethylene oxide will swell in water, the degree of swelling decreasing with increasing temperature. It has now been discovered that polymers used according to the present invention will swell at temperatures below 50° C. by absorbing water as such or from aqueous organic solvent, for example aqueous alcoholic solutions, or formamide, swelling by absorption of up to 1,000 parts per hundred of the original dry volume being attainable, and that, surprisingly, when the swollen polymer is heated, it shrinks, expelling some of the absorbed liquid. This property we believe to provide a counterpart to the function of crystallinity in controlling the behaviour of the polymeric carriers in the dry form and believe it to be responsible for the advantageous pattern of release shown by the polymeric carriers in the wet form as discussed below.

It has been found that both the ability to crystallise, which is of importance in the case of the dry hydrogels, and the ability to show syneresis, which is of importance in the wet hydrogels, is dependent on the equivalent weight of the residues comprising polyethylene oxide in the polymeric carrier. Thus, the presence of a sufficiently high equivalent weight will lead either to the crystallisation of the molecular chains which is present in the dry gels or to the formation of the hydrate chains which are present in the wet gels and which is believed to be responsible for the phenomenon of syneresis exhibited by these gels. We have found that both properties depend on the presence in the polymeric carrier of residues comprising polyethylene oxide units having an equivalent weight of greater than 1,000, for example of 1,200, suitably greater than 1,500, for example of 1,700, 1,800 or more, conveniently of about 2,000 or more and particularly 2,500 or 3,000 or more. Indeed, very high equivalent weights are quite acceptable, the upper limit substantially being governed by the availability of polyethylene oxide of these high equivalent weights; at the present time polymers of equivalent weights of as much as 10,000 being available for use. It is generally the case that unless steps are taken to avoid crystallisation, which would give products of less interest but which are nevertheless not excluded from the scope of the present invention, then the use of residues comprising polyethylene oxide of the equivalent weights indicated will lead to the presence of some proportion of crystallinity in the dry hydrogels. Reduction of the proportion of polyethylene oxide in the polymer through incorporation of high levels of the cross-linking agent or of other components will in general lead to reduction in the level of crystallinity and, accordingly, it is preferred that the proportion by weight of polyethylene oxide of equivalent weight above 1,500 in the polymer is at least 50% and preferably more than this, conveniently greater than 70% and conveniently as high as 75, 80, 85 or 90% or more depending on the individual polymer, for example even up to 96 or 98%.

The controlled release compositions of this invention comprise a polymeric carrier as herein described and a prostaglandin which is usually dispersed throughout the polymeric carrier. Such controlled release compositions can have a variety of effects on the body; for example, they may be useful in the treatment of schizophrenia, particularly $PGE_1$. They are, however, of particular interest in their action upon the female reproductive system of both human and non-human animals. By that action the controlled release compositions of this invention have found use as abortifacients; in the induction of labour; in a contraceptive role; and in the treatment of cervical incompetence, particularly in administration prior to artificial insemination in non-human animals. Both naturally-occuring and synthetic analogues of prostaglandins are of interest.

The natural prostaglandins of importance in reproduction are those of the E and $F_\alpha$ groups (for example $PGE_1$, $PGF_{1\alpha}$, $PGE_2$, $PGF_{2\alpha}$, $PGE_3$ and $PGF_{3\alpha}$), the compounds $PGE_2$ and $PGF_{2\alpha}$ being of particular interest. Examples of synthetic prostaglandins (analogues) include particularly derivatives of $PGE_2$ and $PGF_{2\alpha}$, specific derivatives of clinical promise being 15-methyl-$PGF_2$, $PGF_{2\alpha}$, 16,16-dimethyl-$PGE_2$, and also 16,16-dimethyl-$PGE_2$ parabenzaldehyde semicarbazone ester, 16-phenoxy-17,18,19,20-tetranor-$PGE_2$ and especially 16,16-dimethyl-trans-$\Delta^2$-$PGE_1$ which may very suitably be formulated according to the present invention, for example in the form of an ester such as the methyl ester. Particular prostaglandins may of course be of especial interest for particular applications so that $PGE_2$, for example, is of more interest in the induction of labour whilst 16,16-dimethyl trans-$\Delta^2$-$PGE_1$ is of more interest in inducing abortion. It will be appreciated that the invention will be applicable to subsequently prepared novel prostaglandin derivatives having similar but modified properties, for example greater potency, prolonged action, greater specificity, to those at present known and used as abortifacients. Thus, for example, there is considerable interest in "luteolytic" prostaglandins such as 16-(3-trifluoromethylphenoxy)-17,18,19,20-tetranor-$PGF_{2\alpha}$ and their use in a contraceptive role. It will be appreciated that, if desired, the polymeric carrier may incorporate two or more prostaglandins.

The present invention is not, however, limited to the simple formulation of prostaglandins but is of broad applicability in the formulation of active substances, particularly biologically active substances. Examples of classes of biologically active substances which may be incorporated in compositions of the present invention include pharmaceuticals, bacteriostats, viruscides, fungicides, topical or dermatological agents and enzymes. Of particular interest are compositions of the present invention comprising, as biologically active substances at least one pharmaceutical.

The compositions of this invention thus find wide application in medical and surgical, including veterinary, contexts as well as outside these areas.

There is no necessity for the active substance to be water soluble although it will often possess some degree of water solubility; all that is required is that it is soluble to an extent commensurate with its desired concentration (which, in the case of a biologically active substance is related to this activity) in the controlled release composition of this invention in the water or organic solvent used to swell the polymeric carrier on incorporation of the active substances therein.

Specific classes of drug which may be utilised in a controlled release composition of the invention include abortifacients other than prostaglandins, hypnotics, sedatives, tranquillisers, anti-inflammatory agents, anti-histamines, anti-tussives, anti-convulsants, muscle relaxants, anti-tumour agents; for example those for the treatment of malignant neoplasia, local anaesthetics, anti-parkinson agents, topical or dermatological agents, diuretics, for example those containing potassium, such as potassium iodide preparations, other than those containing prostaglandins, for the treatment of mental illness, for example preparations containing lithium for use in the treatment of manic depression, anti-spasmodics, anti-ulcer agents, preparations containing various substances for the treatment of infection by pathogens including anti-fungal agents, for example metronidazole, anti-parasitic agents and other anti-microbials, anti-malarials, cardiovascular agents preparations containing hormones, for example androgenic estrogenic and progestational hormones, notably steroids such as oestradiol, sympathiomimetic agents, hypoglycaemic agents, contraceptives, nutritional agents, preparations containing enzymes of various types of activity, for example chymotrypsin, preparations containing analgesics, for example aspirin, and agents with many other types of action including nematocides and other agents of veterinary application.

The or each prostaglandin and, optionally, any other active substance may be incorporated into the polymer with this in dispersed form but is more preferably incorporated into the polymeric carrier after this has been formed into an appropriate physical format. Accordingly, the usual procedure for incorporation of the biologically active substance is for the polymer, in suitable physical form, to be swelled using a solution containing the substance to be incorporated. This solution may often be aqueous but may incorporate organic solvents for example, alcohols such as ethyl alcohol in order to solubilise the substance and also in view of the improved swelling characteristics of such mixtures, and in some instances a completely non-aqueous organic solvent may be used, such as chloroform, ethanol/chloroform, tetra-hydronaphthalene, nitrobenzene, methyl benzoate, butyrolactone or benzyl alcohol. After swelling and absorption of the active substance, the release composition may be dried to remove the solvent or alternatively may be used in the swollen form. It has been found that the swelling procedure, and in particular the proportion of swelling relative to the original volume which is allowed to take place, can have a quite significant effect upon the subsequent behaviour of the release composition in vivo, even though it may be dried before use. For example, it has been found that when prostaglandins are incorporated by swelling to a level of 400 parts per hundred of the original dry volume then a release of 60–70% of the prostaglandin content of the release composition can be achieved and in appropriate circumstances in a manner approximately to a linear release rate, over a period of 24 hours. When the swelling is increased to 1000 parts per hundred during the incorporation of the prostaglandin then the proportion of the prostaglandin content released in this way in vivo may be reduced to about 50%. Preferably, therefore, the degree of swelling during incorporation of the biologically active substance lies between 150 parts per hundred and 700 parts per hundred of the original dry volume, particularly between 200 and 500 parts per hundred.

As indicated previously, the polymers used in the present invention are hydrogels which may be used in an initially dry or initially swollen state and the mode of release differs in each case. The dry crystalline gels have the particular property not possessed by rubbery gels that on swelling, for example of a cylindrical pessary of the gel by body fluids, an outer shell of swollen or rubbery form is produced surrounding a core of crystalline material. This leads to certain particular advantages.

Firstly, for an extended period a much more uniform release of the substance is generally achieved in vivo as compared with the usual fairly rapid exponential or $t^{-\frac{1}{2}}$ fall off found with rubbery gels. Moreover, the pattern of release is very largely controlled by the nature of the polymeric carrier rather than the nature of the entire release composition, providing the active substance has a good water solubility, so that the formulation of such release compositions to give a particular release rate is considerably simpified. In the case of active substances of lower water solubility the release may be more dependent on the individual substance.

The wet gels function through the explusion of the active substance from the release composition in a positive in vivo action consequent upon the occurrence of a rise in temperature from that at which the substance is stored and the consequent deswelling of the polymeric carrier releasing solvent and the active substance therefrom. It will be appreciated that this necessitates the incorporation and storage of the active substance at a temperature below that to which the polymeric carrier is subjected in use. Thus, for example, when the active substance is a pharmaceutical the polymer may conveniently be treated at 20° C. or less, for example at a temperature down to 0° C. or even as low as −19° C., with the solution of the pharmaceutical to effect the desired degree of swelling and uptake of the substance. Administration of the release composition so formed to a patient will then cause the temperature to rise to body temperature, which is about 37° C. in a human, and shrinkage of the polymer then occurs with expulsion of the solvent and active substance. In the even of any problems being encountered with respect to stability of the swollen gels, it is always possible to carry out the swelling shortly before use.

The present invention thus further comprises incorporating an active substance into a polymeric carrier comprising residues of equivalent weight greater than 1,000, preferably greater than 1,500, which comprise polyethylene oxide and are cross-linked through urethane groups by swelling of the polymer at one temperature with a liquid medium containing the substance, and thereafter utilising the swollen polymer in an environment at a second, higher, temperature thereby to cause expulsion of liquid medium and active substance from the swollen polymer. Moreover, the invention comprises administering to a human or non-human animal patient a composition comprising a biologically active substance and a polymeric carrier therefor, comprising residues of equivalent weight greater than 1,000, preferably greater than 1,500 which comprise polyethylene oxide and are cross-linked through urethane groups, said composition being of a crystalline and/or swollen form.

Reference has been made previously to the desirability in some instances of removing water extractable material from the polymer. The syneresis effect provides a particularly suitable method for doing this which avoids the problems often encountered in drying down a heavily swollen polymer in an oven, for example cracking of the formed polymer. Thus, the formed polymer may be treated at a temperature below 100° C., for example at about 37° C., with water or an aqueous solvent and the swollen polymer may then be shrunk by heating in the same medium, for example at 100° C. in boiling water, when expulsion of solvent and dissolved soluble material will occur. Final drying may then be effected in an oven, followed by incorporation of the active substance into the polymer.

The detailed nature of the procedure used for incorporating the biologically active substance into the polymeric carrier, including the physical format of the polymeric carrier, is conveniently selected with a view to achieving the desired release characteristics. The polymeric carriers may be used as film or powder but are most often used in the form of a shaped body such as a hollow or blank cylinder, a sphere, a tablet or a slab and the nature of the shape and its dimensions may be selected appropriately. A primary target is to achieve a controlled release over appropriate time period, conveniently of a major proportion, for example 80 or 90%, of the active substance. Release at a substantially constant rate, i.e. approximately to linear release, is an appropriate target in certain instances, for example in the abortifacient use of prostaglandins, and is provided to a considerable degree by the polymeric carriers of the present invention in dry form, when in the form of a slab or flat sheet.

Unusual release profiles may, however, be obtained by utilising polymeric carriers which comprise open cavities, for example hollow cylinders or slabs with one or more holes or hollows in them. It is found that the release profiles of such polymeric carriers can go through a maximum with time. Such geometric control of release profile provide very useful additional means of obtaining and controlling improved release profiles.

It has, however, additionally been found that polymers used in the present invention generally exhibit behaviour at their upper range of swelling which can be of assistance in maintaining a rate approximating to linear release for as long a period as possible. Thus it has surprisingly been found that the polymer, once swollen by a factor of about 10 times, will typically undergo spontaneous shrinkage back to a swelling level of only about 9 times. As the dry polymer swells in use, or as the wet polymer swells further, a boost to the rate of expulsion of the active substance is thereby given just at a time when this rate may be beginning to fall.

In the case of prostaglandins and substances of like activity, release of a large proportion of the active substance over a period of up to about 48 hours, particularly about 18 to 24 hours, is appropriate in abortifacient or labour inducing contexts, although in other contexts a longer period, for example up to 3 or even as much as 10 days may be desirable.

Certain of the areas of pharmaceutical utility for compositions according to the present invention, such as the use of prostaglandins or substances with related actions together with substances having activity against pathogenic micro-organisms, are particularly suited to vaginal administration of the active substance and pessaries are of especial interest in such contexts.

The mode of release from the wet polymeric carriers means that these may be employed in certain particular contexts. An example is in the treatment of maladies wherein a small dose of drug requires to be released into the body each day. The temperature of the human body varies throughout the day, and generally follows a cycle. As the degree of swelling of the polymer is dependent on temperature, a swollen polymeric carrier having a solution of a suitable drug absorbed therein may be implanted into the body, and the polymer will shrink and swell in response to the body temperature fluctuations. During the periods of shrinkage, i.e. the periods or rising temperature, increased portions of the absorbed drug will be ejected from the polymeric carrier into the bloodstream, thus providing a cyclical daily dosage of the drug.

The concentration of the or each prostaglandin incorporated into the controlled release composition of this invention is generally very low, typically no more than 1.0%. Loadings of 0.6% to 0.2% are typical and compositions with loadings of 0.05% or even less can be clinically active.

The concentration of active substance incorporated into the controlled release composition of this invention can range from very high to very low. Thus, if a liquid biologically active material, such as m-cresol which swells the polymer to more than 1000 pph, were used also to swell the polymer, then the active species could comprise more than 90% by weight of the release composition. A liquid which swelled is 1000 pph and contained 25% of a drug could leave a loading of more than 70% of the drug in the dry polymer, and 30% to 70% loadings would be commonly attainable. Much lower loadings, e.g. 1.0% to 0.5% are also readily attainable.

The large degree of polymer swelling which is possible, and the small differences in temperature which occur in natural body temperature cycles, makes it possible for small doses of a drug to be positively ejected into the body daily over a long period of time, and this feature is accordingly of interest in relation to the area, for example, of long-acting contraceptives of low water solubility.

Controlled release compositions of this invention, in dry form, are also of interest in relation to the beneficial effect on the storage stability of potentially unstable compounds such as prostaglandins by incorporation into a crystalline matrix.

The general advantages of the polymeric carriers used in the present invention in the formulation of active substances, as compared with other polymers described in the art for this purpose, may be summarised as follows. The polymers are non-linear, cross-linked, high equivalent weight systems of an essentially insoluble nature as regards both water and a range of organic solvents which show a high degree of swelling with both aqueous and non-aqueous solvents and form tough materials in both the dry and wet forms (although naturally to a lesser extent in the latter case). The polymeric carriers also show a good profile of release which is controlled either by the crystallinity present in the dry gels or the syneresis effect obtainable with the wet polymers.

It will be appreciated that the present invention therefore further include a controlled release composition which comprises an active substance and a polymeric carrier therefor, the carrier comprising polyethylene oxide cross-linked through urethane groups and having the property of possessing crystallinity in the dry form and of exhibiting syneresis in the wet form. The term syneresis as used above means the property of undergoing a substantially greater level of swelling in an aqueous medium at 0° C. than at 100° C.

The invention is illustrated by the following Examples.

PREPARATION OF POLYMERS: EXAMPLE 1

Polyethylene oxide/Methane diphenyl di-isocyanate/Trimethylol Propane Polymer Polyethylene glycol (PEG 6,000, supplied by ICI) is melted and passed through a charcoal column at 80° C. in order to remove acidic contaminants. The product is then dried at 120° C. for 6 hours under vacuum whilst bubbling dry nitrogen through the melt in order to assist the removal of water. The hydroxyl and acid numbers are then determined by the method described in the ASTM (American Society for Testing Materials) Manual D1638, 67T, numbers 93 to 118 to give values of 18.85 and 0.70 respectively (hydroxyl number corrected using acid number=19.55). Using this corrected hydroxyl number the stoichiometric equivalent of 4,4'-diphenyl-methane di-isocyanate (MDI) for 6,000 grams of the product is calculated to be 1.05 moles or 262.5 g.

Purified PEG 6,000 (280.04 g) is treated at 80° C. in a round bottom flask with 2-ethyl-2-hydroxymethylpropane-1,3-diol (trimethylol propane, TMP, supplied by BDH) which has been dried under vacuum (1 mm Hg) at 80° C. for 6 hours and thereafter stored in a desiccator. Pure molten MDI (supplied by ICI and purified by distillation at 2 mm Hg) is added to the mixture of glycols. The whole mixture is briefly stirred for 15 seconds and is then degassed for 2 minutes before pouring into a suitable preheated mould for curing by heating in an oven. The cured polymer, which is an opaque white mass, is stored with the absence of water.

Several molar proportions of TMP are used in the preparation of different polymers. The respective amounts of TMP are 3.13 g, 4.695 g and 6.26 g (0.5, 0.75 and 1.0 molar proportions). The amount of MDI used in each case is 1.05 molar proportions in respect of the PEO and 1.5 molar proportions in respect of the triol. The quantity will accordingly vary, depending on the molar proportion of triol/PEO, the amounts being respectively 21.15 g, 25.5 g and 29.75 g of MDI (1.8, 2.175 and 2.55 molar proportions relative to PEO) for 0.5, 0.75 and 1.0 molar proportions of triol relative to PEO.

EXAMPLE 2

Polyethylene oxide/Methane diphenyl di-isocyanate/1,2,6-Hexane triol Polymer The procedure described above for the PEO/M-DI/TMP polymer is followed but using the following reactants:

| polyethylene glycol (PEG 6,000) | 313.41 g | |
| 1,2,6-hexane triol | 6.7 g | (1 molar proportion) |
| 4,4'-diphenylmethane di-isocyanate | 33.3 g | (2.55 molar proportions) |

The cured polymer is obtained in an exactly analogous fashion.

EXAMPLE 3

Polyethylene oxide/Methane diphenyl di-isocyanate/Phloroglucinol Polymer

The procedure described above for the PEO/M-DI/TMP Polymer is followed but using the following reactants:

| polyethylene glycol (PEG 6,000) | 301.4 g | |
| phloroglucinol | 6.3294 g | (1 molar proportion) |
| 4,4'-diphenylmethane di-isocyanate | 32.023 g | (2.55 molar proportions) |

The cured polymer is obtained in an exactly analogous fashion.

EXAMPLE 4

Polyethylene oxide/Methane diphenyl di-isocyanate Polymer (A) Polyethylene glycol (325.25 g, PEG 6,000) purified as described previously is placed in a beaker at 80° C. and crude MDI (total of 21.24 g corresponding to the stoichiometric equivalent required by the glycol of 16.34 g plus an excess of 4.9 g, being 30% of this amount, supplied by ICI as Suprasec-DN) is added to it whilst maintaining the temperature close to 80° C. and with continuous stirring. Once the addition is complete the homogeneous mixture is poured into a suitable preheated mould for curing by heating in an oven. The cured polymer, which is a dark brown mass, is stored in the absence of water.

(B) The procedure described under (A) is repeated but using polyethylene glycol (PEG 4,000, supplied by ICI) which is purified as described previously for PEG 6,000, having a hydroxyl number of 27.11, an acid number of 0 and a corrected hydroxyl number of 27.11.

The following proportions of reactants are employed:

| Polyethylene glycol | 251.47 g |
| crude MDI | 22.71 g |
| (stoichiometric equivalent of 17.47 g plus the 30% excess of 5.24 g) | |

The cured polymer is obtained in an exactly analogous fashion.

Examples 5 to 7 below illustrate the reduction in crystallinity in the dry gel with decreasing equivalent weight. The preparative method was in all cases analogous with the following procedures, referred to #3 of Example 5.

1.615 g of 1,2,6-hexanetriol is added to 100 g of polyethylene oxide of number average molecular weight 8,300 (Carbowax 6,000 ex Union Carbide) in a beaker and both are allowed to stand at 80° C. 7.527 g of pure molten MDI is then poured into the mixture which is then vigourously stirred for 30 seconds before being poured into a mould which was preheated at 85° C. The mould is placed in an oven at 85° C. for four hours to cure. After curing the mould is next cooled and the opaque off-white block of polymer was removed and stored away from moisture.

EXAMPLE 5

| Moles triol[1] moles PEO[2] | Weight (g) PEO | Weight (g) triol | Weight (g) MDI | Physical Appearance |
| --- | --- | --- | --- | --- |
| 0.5 | 100 | 0.8075 | 5.2705 | White brittle opaque |
| 0.75 | 100 | 1.2113 | 6.3992 | " |
| 1.0 | 100 | 1.615 | 7.527 | " |
| 1.25 | 100 | 2.0189 | 8.6563 | " |
| 1.5 | 100 | 2.4227 | 9.7848 | " |
| 1.75 | 100 | 2.826 | 10.9119 | " |
| 2.0 | 100 | 3.23 | 12.041 | " |
| 3.0 | 100 | 4.8454 | 15.5556 | " |
| 4.0 | 100 | 6.460 | 21.068 | almost transparent |

EXAMPLE 6

| Moles triol[1] moles PEO[3] | Weight (g) PEO | Weight (g) triol | Weight (g) MDI | Physical Appearance |
| --- | --- | --- | --- | --- |
| 0.25 | 100 | 1.0457 | 10.73044 | opaque |
| 0.35 | 120.0 | 1.8305 | 14.5853 | opaque rubbery |
| 0.5 | 100.0 | 2.092 | 13.6525 | opaque rubbery |
| 0.75 | 100.0 | 3.137 | 16.5752 | rubbery |
| 1.0 | 100.0 | 4.184 | 19.4978 | slightly transparent |
| 1.25 | 100.0 | 5.2284 | 22.4197 | slightly transparent |
| 1.5 | 120.0 | 7.529 | 30.4112 | transparent |
| 1.75 | 100.0 | 7.3219 | 28.2755 | " |
| 2.0 | 100.0 | 8.368 | 31.1989 | " |

EXAMPLE 7

| Moles triol[1] moles PEO[4] | Weight (g) PEO | Weight (g) triol | Weight (g) MDI | Physical Appearance |
| --- | --- | --- | --- | --- |
| 0.3 | 100.0 | 2.5002 | 22.532 | opaque rubbery |
| 0.4 | 100.0 | 3.3336 | 24.8697 | opaque rubbery |
| 0.5 | 100.0 | 4.1675 | 27.1984 | transparent rubbery |
| 0.6 | 100.0 | 5.0004 | 29.5278 | transparent rubbery |
| 0.75 | 100.0 | 6.2506 | 33.0219 | transparent rubbery |
| 1.0 | 100.0 | 8.3341 | 38.8447 | transparent rubbery |
| 1.25 | 100.0 | 10.4177 | 44.6679 | transparent rubbery |
| 1.5 | 100.0 | 12.5012 | 50.4908 | transparent rubbery |
| 1.75 | 100.0 | 14.5847 | 56.3138 | brittle |
| 2.0 | 100.0 | 16.6682 | 62.136 | " |

[1]tril is 1,2,6-hexanetriol
[2]PEO is Carbowax 6,000 (Union Carbide) $\overline{M}_n$ = 8300
[3]PEO is Carbowax 4,000 (Union Carbide) $\overline{M}_n$ = 3200
[4]PEO is Carbowax 1,500 (Union Carbide) $\overline{M}_n$ = 1600

Example 8 and 9 below illustrate the preparation of polymers using aliphatic di-isocyanates. These are hexamethylene di-isocyanate (ex Bayer) and methane dicyclohexane di-isocyanate (Hylene W ex Du Pont). A catalyst, in this case from 0.4 to 0.6% W/W FeCl$_3$, was used to lower the reaction time.

EXAMPLE 8

| Moles triol[1] moles PEO[2] | Weight (g) PEO | Weight (g) triol | Weight (g) Hylene | Weight (g) Hexamethylene di-isocyanate |
| --- | --- | --- | --- | --- |
| 1.0 | 100 | 1.61 | 7.91 | — |
| 1.0 | 100 | 1.61 | — | 5.06 |
| 0.75 | 100 | 1.21 | 6.72 | — |
| 0.75 | 100 | 1.20 | — | 4.30 |
| 0.5 | 100 | 0.81 | 5.53 | — |
| 0.5 | 100 | 0.81 | — | 3.54 |

EXAMPLE 9

| Moles triol[1] moles PEO[2] | Weight (g) PEO | Weight (g) triol | Weight (g) Hylene | Weight (g) Hexamethylene di-isocyanate |
| --- | --- | --- | --- | --- |
| 1.0 | 100 | 2.090 | 14.329 | — |
| 1.0 | 100 | 2.092 | — | 9.174 |
| 0.75 | 100 | 3.138 | 16.956 | — |
| 0.75 | 100 | 3.138 | — | 10.856 |
| 0.5 | 100 | 4.184 | 19.879 | — |
| 0.5 | 100 | 4.184 | — | 12.727 |

EXAMPLE 10

Polymer Incorporating the Prostaglandin PGE$_2$ (A) Cylinders of polymers prepared as described above in Example 1 using 0.75 molar proportions of TMP are produced as described in Example 1. The cylinders are not subjected to the aqueous ethanol extraction procedure but are directly subjected to treatment with a solution of 17.1 mg of $^3$H labelled PGE$_2$ (ca. 10 μCi) in 20 g of 7:3 w/w ethanol/water to effect swelling at ambient temperature over 24 hours. Typically an increase in the weight of the cylinders of 3.52 g from 0.71 g dry weight to 4.23 g wet weight is observed corresponding to an uptake of 3.03 mg PGE$_2$ per cylinder. (The $^3$H activity of the solution used for swelling remains constant throughout.) The swollen cylinders are vacuum dried for 48 hours at ambient temperature.

In vitro studies on the release of PGE$_2$ from the dry cylinders into pH 7.4 phosphate buffer at 37° C. through measurement of the $^3$H activity typically show a half life for release of the drug which is of the order of 20 hours although the exact value will depend on the dimensions of the cylinder.

(B) The procedure described in (A) is followed but the swollen cylinders obtained after 24 hours treatment with the PGE$_2$ solution are not dried but are tested directly for the release of PGE$_2$ into pH 7.4 phosphate buffer at 37° C. In this instance a typical half life is of the order of 10 hours.

In variants of the above procedure one of the polymers (2) to (4) described above is substituted for the polymer (1).

EXAMPLE 11

Polymer Incorporating the Prostaglandin 16,16-Dimethyl-PGE$_1$ methyl ester

Cylinders of polymer prepared as described above in Example 1 using 0.75 molar proportions of TMP are prepared as described in Example 1. The cylinders are not subjected to the aqueous ethanol extraction procedure but are directly subjected to treatment with a solution of 2 mg of $^3$H labelled (ca 0.5 μCi)16,16-dimethyltrans-Δ²-PGE₁ in 4 g of 1:1 w/w chloroform/ethanol to effect swelling at ambient temperature over 24 hours. A typical increase in the weight of the cylinders of 2.05 g from 0.72 g to 2.77 g is observed, corresponding to an uptake of 1.03 mg of 16,16-dimethyl-trans-Δ²-PGE₁ methyl ester per cylinder. The swollen cylinders are dried in a stream of oxygen free nitrogen for 48 hours at ambient temperature.

In vitro studies on the release of the prostaglandin from the dry cylinders into pH 7.4 phosphate buffer through measurement of the ³H activity typically show a half life of the order of 95 hours although the exact value will depend on the dimensions of the cylinder.

In variants of the above procedure one of the polymers (2) to (4) described above is substituted for the polymer (1).

EXAMPLE 12

Polymer Incorporating the Prostaglandin PGE₂

A block of polymer prepared as described in Example 2 above but using 1 molar PEG 8,300 (or Carbowax 6,000), 1 molar 1,2,6 hexane triol and the molar equivalent of MDI is then cut into slices 2.6 mm thick. Strips 10 mm wide by 30 mm length are cut from the slices, and the corners are trimmed to form lozenge shaped pessaries average weight 0.92 g. The soluble extractable material is then removed by swelling in regularly replaced distilled water at 37° C. over 3 days when the extract analysed by UV spectrophotometer at 245 nm measures less than 0.5% per day. The water is then brought to the boil to sterilise and synerise the samples, which are next air dried and finally vacuum dried at room temperature to constant weight.

19.08 g Prostin E2 at a 1% w/v solution in dephydrated ethanol is weighed. This is equivalent to 24.15 ml and therefore 0.2415 g PGE₂. A further 55.31 g ethanol is added, then 54.39 g chloroform to give a final 1/1, w/w, CHCl₃/C₂H₅OH containing 241.5 mg PGE₂ in 108.78 g solution.

25 of the pessaries (2.6 mm×10 mm×30 mm total weight 23.02 g) are then put in a polythene bag. The swelling solution is added, and the bag is sealed. The pessaries are then allowed to swell in the PGE₂ solution for 20 hours by which time nearly all the solution has been absorbed by the polymer. The bag is cut open and the swollen pessaries are removed and weighed. Uptake of solution: 104.75 g. Average PGE₂ content/pessary 9.3 mg.

The swollen pessaries are then vacuum dried at room temperature.

Release of PGE₂ from a Dry Pessary

An identical pessary is prepared with the addition of 1 μCi ³H labelled PGE₂ to study in vitro the release of PGE₂ from the dry pessary into phosphate buffer pH 7.4 at 37° C. through measurement of ³H activity of the buffer solution which is replaced by fresh buffer at regular intervals. The half life $t_{\frac{1}{2}}$ of the PGE₂ in this polymer is 7 hours.

This result, and the results from other preparations with different thickness of pessary show the half life of PGE₂ in the polymer is directly proportional to the thickness, as shown in the Table below:

| Thickness 1 (mm) | 1² (mm²) | $t_{\frac{1}{2}}$ (hours) |
|---|---|---|
| 1.2 | 1.4 | 1.4 |
| 1.5 | 2.3 | 2.4 |
| 1.7 | 2.9 | 2.7 |
| 2.6 | 6.7 | 7.0 |
| 2.9 | 8.4 | 8.0 |
| 3.4 | 11.6 | 12.0 |

Release of PGE₂ from a Fully Swollen Pessary

To study the release of PGE₂ from a fully swollen pessary into phosphate buffer pH 7.4 at 37° the polymer is swollen in an ethanol/water solution of PGE₂ of 0.87 g C₂H₅OH solution of 1% w/v Prostin E2 contains 11 mg PGE₂ 0.09 g C₂H₅OH containing 1 μCi of ³HPGE₂ is added, then 3.56 g H₂O. A slice of polymer 3.1 mm×10 mm×30 mm weighing 1.13 g is added to the prepared PGE₂ solution in 3.7/1, w/w, water/ethanol in a polythene bag. The bag is sealed and the polymer allowed to swell over 20 hours. The swollen polymer slice is then removed and the surface wiped dry with a tissue before weighing. Uptake of solution: 4.44 g i.e. almost all the PGE₂ is contained in the swollen gel. The pessary is rinsed in distilled water and then transferred to phosphate buffer solution pH 7.4 at 37° C. The release of PGE₂ into the surrounding solution is measured by frequent regular replacement of the buffer and counting the activity of ³H in the withdrawn solution. From these measurements the half life $t_{\frac{1}{2}}$ of PGE₂ in the swollen pessary is calculated as 2.7 hours. It is also possible to calculate the diffusion coefficient of PGE₂ in the swollen gel $D = 0.83 \times 10^{-6}$ cm² sec⁻¹.

The results for the half life of 3 different thicknesses of pessary are given in the Table below:

| Thickness mm | 1² (mm²) | $t_{\frac{1}{2}}$ (hours) |
|---|---|---|
| 1.2 | 1.4 | 0.7 |
| 2.4 | 5.8 | 2.0 |
| 3.1 | 9.6 | 2.7 |

It will be seen that the half life of PGE₂ in the fully swollen device is approximately half of the half life in the initially dry device. In addition the fully swollen devices do not provide the desirable reasonably constant period of the rate of release.

EXAMPLE 13

Polymer Incorporating 16,16 dimethyl PGE₂ methyl ester 2 mg ³H labelled 16,16-dimethyl PGE₂, methyl ester Ono 802 ex May and Baker is dissolved in 0.67 g ethanol C₂H₅OH, 0.67 g chloroform CHCl₃ is added. A slice of the polymer 1 mm×11 mm×22 mm weighing 0.2678 g is added to the Ono solution in a polythene bag which is then sealed. After 6 hours swelling the bag is cut open and the swollen gel is weighed. Uptake 0.97 g solution i.e. 1.45 mg Ono. The sample is then dried and the in vitro release of Ono into phosphate buffer pH 7.4 at 37° is measured as in Ex. 12. The half life of Ono in this sample is 6.3 hours. The results for 3 different thicknesses of polymer sample are given to the Table.

| Thickness (mm) | $l^2$ (mm$^2$) | $T_{\frac{1}{2}}$ (hours) |
| --- | --- | --- |
| 0.25 | 0.0625 | 0.5 |
| 0.65 | 0.423 | 3.0 |
| 1.00 | 1.00 | 6.3 |

The half life $t_{\frac{1}{2}}$ of Ono in the polymer is therefore directly proportional to the square of the thickness.

EXAMPLE 14

Polymer Incorporating 16,16 dimethyl prostaglandin E$_2$ benzaldehyde semi-carbazone 83 mg PG ester (ex Upjohn) is dissolved in 5.61 g ethanol and 5.61 g chloroform.

15 slices of the polymer 0.25 mm×10 mm×50 mm weighed 2.61 g Average weight/slice 0.17 g. The polymer is swollen in the PG ester solution as in Ex. 13 only 2 hours is sufficient time for complete swelling of PED of this thickness. 83 mg PG ester in 15 samples i.e. 5.5 mg PG ester/sample.

An identical sample to 3a is prepared with the addition of 0.6 µCi $^3$H labelled PG ester and as in Example 12 the release of PG ester from the slice is measured by replacing the buffer solution at regular intervals and counting the activity of the solution withdrawn. For such a thin sample the release is essentially that of a fully swollen device containing a dispersion rather than a solution of a low solubility prostaglandin analogue. The rate of diffusion is effected by the concentration of the ester in the encompassing solution.

During the first 12 hours a fairly steady release rate of 85 g/hour was observed for 4 sample taken at 3 hourly intervals. This then dropped to 13 µg/h overnight and recovered to 50 µg/hour on day 2. This pattern continued for 2 weeks.

EXAMPLE 15

Polymer Incorporating N methanesulphonyl 15z, 11$\alpha$, 13E 15$\alpha$)-9-Oxo-11,15-dihydroxy-16-phenoxy-w-tetranor-prosta-5,13 dien-1-amide 555 mg of this prostaglandin analogue (ex Schering) is dissolved in 2.88 g chloroform and 2.88 g ethanol together with 1 µCi $^3$H labelled analogue.

A slice of PEO 1.2×24×40 mm weighing 1.3083 g is added to the solution in a polythene bag which is then sealed. After 6 hours the bag is opened and the swollen polymer weighs 5.56 g, the prostaglandin content being calculated as 4.06 mg.

After drying to constant weight the diffusion of the drug into buffer solution at pH 7.4 at 37° C. is measured as in Example 12. The half-life of the drug in the pessary is 3.7 hours.

Clinical Studies

Hydrogel vaginal pessaries, formulated as above, each containing PGE$_2$ 10 mg, have been evaluated clinically in a pilot study. The clinical experience accorded well with in vitro release studies.

Appreciable uterine activity, not requiring analgesia, was generated in 1-2 hours and maintained or gradually increased, with significant 'ripening' of the cervix in all cases.

Patients with average or favourable induction prospects became established in labour and made good progress, with successful vaginal delivery, as a result of PGE$_2$ treatment alone and without the need for orthodox induction.

In unfavourable patients the latent phase of labour was expectedly longer but cervical 'ripening' was progressive and all were established in labour following PGE$_2$ treatment.

Induction of abortion has been effected using from 1 to 2.5 mg of 16:16-dimethyl-trans-$\Delta^2$-PGE$_1$.

We claim:

1. A process for the preparation of a controlled release composition, which composition comprises a prostaglandin and a polymeric carrier therefor, said polymeric carrier comprising residues having a ratio of number average molecular weight to functionality greater than 1,000 which comprise polyethylene oxide and are cross-linked through urethane groups, said process comprising:
   (i) contacting said polymeric carrier with a solution of a prostaglandin and permitting said polymeric carrier to swell therein; and
   (ii) removing the swollen polymeric carrier from said solution thereby obtaining a controlled release composition comprising the prostaglandin.

2. The process of claim 1, wherein, subsequent to removal from said solution, said swollen polymeric carrier is dried.

3. The process of claim 1, wherein the swelling of said polymeric carrier is from 200 to 700 parts by volume per hundred of the initial dry volume.

4. The process of claim 1, wherein said swelling is effected at a temperature of from −20° C. to +20° C.

5. The process of claim 1, wherein said controlled release composition comprises a prostaglandin and a polymeric carrier therefor comprising residues which are cross-linked through urethane groups, or analogues thereof, and which comprise polyethylene oxide having a ratio of number average molecular weight to functionality greater than 1,500, the degree of cross-linking being such that there is at least one cross-linking point per ten residues comprising the said polyethylene oxide but such that the proportion of the said polyethylene oxide is greater than 50% by weight of the polymeric carrier which, when prostaglandin-free, is a hydrogel, in the dry form at 20° C. contains crystalline regions, and exhibits syneresis in the wet form.

6. The process of claim 1, wherein said controlled release composition comprises a prostaglandin and a polymeric carrier therefor comprising residues which are cross-linked through urethane groups, or analogues thereof, and which comprise polyethylene oxide having a ratio of number average molecular weight to functionality greater than 1,500, the degree of cross-linking being such that there is at least one cross-linking point per ten residues comprising the said polyethylene oxide but such that the proportion of the said polyethylene oxide is greater than 50% by weight of the polymeric carrier which, in the presence of said prostaglandin, is a hydrogel, in the dry form at 20° C. contains crystalline regions, and exhibits syneresis in the wet form.

7. The process of claim 5, said controlled release composition further comprising an additional drug other than a prostaglandin.

8. The process of claim 6, said controlled-release composition further comprising an additional drug other than a prostaglandin.

9. The process of claim 5, wherein the polyethylene oxide has a ratio of number average molecular weight to functionality greater than 2,000.

10. The process of claim 5, wherein the polyethylene oxide is the reaction product of a mixture comprising (i) an aliphatic or aromatic compound which is di-, tri- or tetra-substituted by at least one hydroxyl, carboxyl, amino or mercapto group with (ii) ethylene oxide.

11. The process of claim 10, wherein component (i) comprises a di- or tri- hydroxyl-substituted aliphatic compound.

12. The process of claim 5, wherein the degree of cross-linking of the polymeric carrier is such that there is at least one cross-linking point per five residues comprising the said polyethylene oxide.

13. The process of claim 5, wherein the degree of cross-linking of the polymeric carrier is such that there is at least one cross-linking point per residue comprising the said polyethylene oxide.

14. The process of claim 5, wherein the degree of cross-linking of the polymeric carrier is such that the proportion of the said polyethylene oxide is greater than 70% by weight of the polymeric carrier.

15. The process of claim 5, wherein the degree of cross-linking of the polymeric carrier is such that the proportion of the said polyethylene oxide is greater than 80% by weight of the polymeric carrier.

16. The process of claim 5, wherein the polymeric carrier comprises up to 20% by weight of an additional polyalkylene oxide.

17. The process of claim 5, wherein the polymeric carrier comprises up to 20% by weight of an additional polyethylene oxide having a ratio of number average molecular weight to functionality not greater than 1000.

18. The process of claim 5, wherein the polymeric carrier comprising up to 30% of its weight of a water-extractable fraction.

19. The process of claim 5, wherein the amount of water-extractable fraction has been reduced to no more than 5% of the polymeric carrier.

20. The process of claim 5, wherein the prostaglandin is naturally-occurring prostaglandin of the E and $F_\alpha$ groups.

21. The process of claim 20, wherein the prostaglandin is $PGE_2$ or $PGF_{2\alpha}$.

22. The process of claim 5, wherein the prostaglandin is a synthetic analogue.

23. The process of claim 22, wherein the prostaglandin is 15-methyl-$PGF_{2\alpha}$, 16,16-dimethyl-$PGE_2$, 16,16-dimethyl-$PGE_2$ parabenzaldehyde semicarbazone ester, 16-phenoxy-17,18,19,20-tetranor-$PGE_2$, 16,16-dimethyl-trans-$\Delta^2$-PGE, and its methyl ester or 16-(3-trifluoromethylphenoxy)-17,18,19,20-tetranor-$PGF_{-2\alpha}$.

24. The process of claim 5, wherein said composition is in the shape of a cylinder, film or slab.

25. The process of claim 24, wherein the cylinder is hollow or the film or slab has at least one hole or hollow therein to modify the release properties.

26. The process of claim 5, said composition for use as an abortifacient.

27. The process of claim 5, said composition for use in the induction of labor.

28. The process of claim 5, said composition for use as a contraceptive.

29. The process of claim 5, said composition for use in the treatment of schizophrenia.

30. The process of claim 5, said composition for use in the treatment of cervical incompetence in livestock.

* * * * *

UNITED STATES PATENT AND TRADEMARK OFFICE
CERTIFICATE OF CORRECTION

PATENT NO. : 5,017,382
DATED : May 21, 1991
INVENTOR(S) : Mostyn P. Embrey et al.

It is certified that error appears in the above-identified patent and that said Letters Patent is hereby corrected as shown below:

Title page item (30):

The Foreign Application Priority Data has been omitted, should be, --March 21, 1979 [UK] United Kingdom ............ 7909853--.

Signed and Sealed this

Fifteenth Day of December, 1992

Attest:

DOUGLAS B. COMER

*Attesting Officer*      *Acting Commissioner of Patents and Trademarks*